US011391735B2

(12) United States Patent
Song

(10) Patent No.: US 11,391,735 B2
(45) Date of Patent: Jul. 19, 2022

(54) METHODS FOR IMPROVING THE DYNAMIC RANGE OF BIOLOGICAL ASSAYS

(71) Applicant: AimPlex Biosciences, Inc., Pomona, CA (US)

(72) Inventor: Yong Song, Pomona, CA (US)

(73) Assignee: AIMPLEX BIOSCIENCES, INC., Pomona, CA (US)

( * ) Notice: Subject to any disclaimer, the term of this patent is extended or adjusted under 35 U.S.C. 154(b) by 995 days.

(21) Appl. No.: 16/115,703

(22) Filed: Aug. 29, 2018

(65) Prior Publication Data
US 2019/0072548 A1 Mar. 7, 2019

Related U.S. Application Data

(60) Provisional application No. 62/554,889, filed on Sep. 6, 2017.

(51) Int. Cl.
*G01N 33/543* (2006.01)
*C12M 3/06* (2006.01)
*C12M 1/12* (2006.01)

(52) U.S. Cl.
CPC ....... *G01N 33/54386* (2013.01); *C12M 23/16* (2013.01); *C12M 25/01* (2013.01); *B01L 2200/027* (2013.01); *B01L 2300/0819* (2013.01)

(58) Field of Classification Search
CPC ........... B01L 2300/0819; C12M 23/16; C12M 25/01; C12Q 1/6837; C12Q 2565/629; G01N 33/54386; G01N 33/48; G01N 33/53
See application file for complete search history.

(56) References Cited

U.S. PATENT DOCUMENTS

| 6,551,788 | B1 | 4/2003 | Bell |
| 7,604,956 | B2 | 10/2009 | Drukier |
| 7,723,127 | B2 | 5/2010 | Talebpour et al. |
| 9,671,398 | B2 | 6/2017 | Campbell |
| 2004/0126899 | A1 | 7/2004 | Lee |

(Continued)

FOREIGN PATENT DOCUMENTS

| GB | 2510653 | 8/2014 |
| WO | 2017034925 | 3/2017 |

*Primary Examiner* — Michael L Hobbs
(74) *Attorney, Agent, or Firm* — Fish IP Law, LLP

(57) ABSTRACT

Compositions and methods are provided that extend the range of biological assays, such as immunoassays. In one embodiment a plurality of discrete test sites are used. Data for the proportion of test sites that indicate the presence of the analyte of interest and data that provides a statistical value for a signal generated by the population of discrete test sites is gathered. The results of these digital and statistical approaches are aggregated to provide an extended dynamic range. In another embodiment two or more reagent additions are provided in a serial fashion to a single test site or vessel. Such additions present different reagent sets with different dilutions of the same sample, and permit simultaneous characterization of both high and low abundance analytes in a single multiplexed assay while avoiding the high dose hook effect observed for high abundance analytes at low sample dilutions. These approaches can be combined to provide further improvements in dynamic range.

19 Claims, 8 Drawing Sheets

(56) References Cited

U.S. PATENT DOCUMENTS

| | | |
|---|---|---|
| 2010/0075862 A1 | 3/2010 | Duffy |
| 2012/0308997 A1 | 12/2012 | Ruan |
| 2014/0065722 A1 | 3/2014 | Goix |
| 2015/0046114 A1 | 2/2015 | Brueckner |
| 2015/0293102 A1 | 10/2015 | Shim |
| 2018/0353913 A1* | 12/2018 | Link ................ B01L 3/502761 |

* cited by examiner

METHODS FOR IMPROVING THE DYNAMIC RANGE OF BIOLOGICAL ASSAYS

This application claims the benefit of U.S. Provisional Application No. 62/554,889, filed on Sep. 6, 2017. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is biological assays, in particular immunoassays.

BACKGROUND

The background description includes information that may be useful in understanding the present invention. It is not an admission that any of the information provided herein is prior art or relevant to the presently claimed invention, or that any publication specifically or implicitly referenced is prior art.

Bioassays, such as immunoassays (for example, EIAs, FIAs, etc.), nucleic acid amplification assays (such as rtPCR, linear amplification assays, etc.), and cell-based assays are a mainstay of modern biological research and clinical practice. Historically these have been performed by treating a sample with an analyte-specific reagent and obtaining a reading of signal intensity (for example, absorbance, fluorescence intensity, luminescence intensity, etc.) from the bulk mixture. This signal intensity that is compared to a standard or dose/response curve of signal intensities obtained from bulk mixtures prepared from similar samples treated with the same reagents in order to derive the concentration of an analyte of interest. In the case of immunoassays such analyte-specific reagents typically include antibodies or antibody fragments that form specific, detectable complexes with the analyte of interest. The dynamic range of such immunoassays is generally limited to about two orders of magnitude. In some applications, however, the range of concentration for an analyte can extend beyond this range. Similarly, in multiplexed assays the concentration ranges for individual analytes can vary widely.

Attempts have been made to develop bioassays with extended measuring or dynamic ranges. For example, U.S. Pat. No. 6,551,788, to Bell, describes a fluorescence-based immunoassay in which particles of different sizes are used as initial capture phases. The patent states that large particles provide more efficient capture of analyte molecules at low concentration than small particles; unfortunately it does not provide either a theoretical framework or data to support this assertion.

United States Patent Application No. 2014/0065722, to Goix et al., describes a somewhat similar approach in which different populations of particles are coupled with either low affinity or high affinity antibodies directed to the same analyte and used as a capture phase. The different particle populations are read separately to produce distinct dose/response curves that can be used to provide an extended measuring range. United States Patent Application Publication No. 2015/0046114, to Dowell et al., describes a similar approach, in which a common capture antibody is used in combination with different labeling antibodies having different affinities for the analyte in a sandwich immunoassay. These approaches, however, require the availability of antibodies having the same specificity and significantly different affinities, which may not be available for an analyte of interest.

In another approach, the use of testing devices that incorporate physically distinct zones or sensors with different binding affinities for an analyte of interest have been proposed. For example, U.S. Pat. No. 9,671,398 (to Campbell, et al.) describes the use of two different immunosensors, one constructed to demonstrate attenuated binding for an analyte relative to the other, to derive overlapping dose/response curves that provide an effectively extended measuring range. The construction of such a device, however, is complex, and becomes increasingly complex when applied to multiplex assays.

In another approach described in U.S. Pat. No. 7,604,956, to Drukier, an extended measuring range is achieved by systematically reducing sources of background noise in an otherwise conventional assay. This reduction in background noise effectively increases the sensitivity of the assay without impacting assay performance at high analyte concentration, resulting in an increased dynamic range. It is not clear, however, if the approaches used to minimize sources of background noise are applicable to a wide range of biological assays. Also, since the approaches to minimize sources of background noise are specific for each analyte it seems unlikely that this approach would be useful for multiplex assays.

In still another approach, described in U.S. Pat. No. 7,723,127 (to Talebpour and Leanord), immunoassays are performed using multiple additions of a sample containing the analyte of interest to a capture reagent. The latter addition is performed using a large volume that dilutes the capture reagent. The resulting composite dose/response curve is intermediate between that generated using either the small initial sample volume or the total sample volume applied as a single bolus. However, while this is positioned as providing a dose/response curve with an extended dynamic range the comparative data provided shows significant response to a broader range of analyte concentrations than the composite dose/response curve provided by separate additions. The extended measuring range reported appears to the result of using an unconventional calculation for minimal detectable dose that selects this value based on a signal that is 10% of the maximum observed signal, rather than the ability to distinguish the observed signal over that achieved with a blank sample.

More recently various techniques have been made to exploit the ability to encode individual occurrences of results of within such assays, particularly in the case of multiplexed assays. For example, a multiplexed immunoassay can be performed using a two-dimensional surface microarray (which provides positional encoding of individual results) or a suspension array of microscopic beads (which can be encoded using dyes, fluorophores, etc. that are distinct from those used to provide analyte-specific results). Such methods are commonly used in multiplexed assays, as the encoding of the results provides a means for distinguishing between the results of different assays performed simultaneously on the same sample. Even without multiplexing, however, deriving quantitative results from such encoded results is challenging. In order to scale properly individual coded results are typically provided over a relatively small and discrete region, for example the surface of an individual microscopic bead or an individual printed "spot" on a microarray. Historically analysis of a single, discrete encoded result has not provided sufficiently accurate results for quantitation. Statistical approaches have been applied to aggregated data from multiple discrete encoded results in order to provide quantitation.

In one approach, the signal intensities from a large number of individual, discrete test regions is measured and used to generate a frequency distribution on intensity values. Typically the mean or median value of the distribution is utilized as the value associated with the analyte concentration for that sample. For example, United States Patent Application No. 2012/0308997 (to Ruan et al) describes a method in which an immunoassay is performed using a population of particles. A distribution of the signal intensity from the test particles is used to calculate a mean signal intensity, which is in turn used to derive the concentration of analyte in the test sample. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. In such approaches, however, assay sensitivity is essentially both mean signal intensity and the variation found within that distribution (i.e. the signal to noise ratio). Since the signal to noise ratio is low at low analyte concentrations the sensitivity of assays using this approach is necessarily limited.

In another approach, individual, discrete test regions are categorized in a binary fashion as either 'positive' (i.e. indicative of the presence of the analyte) or negative (i.e. indicative of the absence of the analyte). In such a "digital" approach the relative proportion of positive to negative test regions is utilized to derive a concentration of the analyte for that sample, typically by comparison to a dose/response curve generated using samples containing known analyte concentrations. For example, Great Britain Patent No. 2510653 (to Shim et al.) describes a method in which individual femtodroplets in an oil:water emulsion prepared using a test sample are categorized as either containing a β-galactosidase marker or not based on enzyme activity. The amount of the β-galactosidase marker present in the test sample is determined by the ratio of positive femtodroplets to negative femtodroplets as determined from an image of a monolayer of such droplets. Similarly, United States Patent Application Publication No. 2015/0293102 (to Shim) describes various immunoassay using fluorescent or enzyme-labeled antibodies in immunoassays performed within femtodroplet suspensions, where the proportion of positive to negative droplets is used to derive the concentration of analyte in the test sample. United States Patent Application Publication No. 2004/0126899 (to Lee and Yanavich) describes the use of a fixed quantity of magnetic particles that form relatively stable complexes with a porous solid phase if the analyte is present. Negative particles that do not form complexes with the solid phase are removed by the application of weak magnetic field and quantitation is provided by enumeration of the remaining bound particles. United States Patent Application Publication No. 2010/075862 (to Duffy et al) describes the use of a complex array of optical fibers that terminate in test areas. An immunoassay is performed on the coated terminus of the fibers, and results determined to be positive or negative for each fiber based on signal intensity. The proportion of positive fibers is utilized to determine the analyte concentration of the test sample. International Patent Application Publication No. WO 2017/034925 (to Zur Megede and Karlin-Neumann) describes a "digital readout assay" in which multiple "partitions" are identified and categorized as positive (containing a label used to indicate the presence of the analyte) or negative (lacking said label). The proportion of positive partitions to negative partitions is used to derive the concentration of analyte present in the test sample. Unfortunately the dynamic range of assays utilizing such an approach is essentially a function of the occupancy of the discrete test regions used, with the upper limit being reached at or near full occupancy. As a result the dynamic range of such assays is necessarily limited.

Thus, there is still a need for a method for improving the dynamic range of biological assays.

SUMMARY OF THE INVENTION

The inventive subject matter provides compositions and methods that extend the dynamic range of biological assays.

One embodiment of the inventive concept is a method for quantifying results derived from a biological assay (such as an immunoassay, a nucleic acid amplification assay, an enzyme assay, and/or a biological activity assay) by performing a first biological assay directed to a first analyte on a sample using a plurality of first discrete test sites, where the first biological assay provides a change in a first signal (such as fluorescence, enzyme activity, absorbance, phosphorescence, and/or luminescence) that indicates the presence of the first analyte. A plurality of quantities representing this first signal are obtained, where each of the plurality of quantities is associated with a value for first signal observed from an individual test site from among the first discrete test sites. A first proportion that includes an enumeration of the first discrete test sites having a signal that indicates the presence of the analyte in the sample is determined. In addition, a statistical distribution of the plurality of quantities derived from the first discrete test sites is used to derive an overall statistical value for the first signal. The mass of the first analyte in the sample is determined using the first proportion when this first proportion falls within a first cutoff range, and is determined using the statistical value of the first signal when the first proportion falls outside of the first cutoff range. In some embodiments such a cutoff range is selected to delineate a population in which less than 90% of the first discrete test sites include the first analyte.

In some embodiments a second biological assay is performed in concert with the first biological assay to quantify a second analyte, in a similar fashion, using a second set of discrete test sites. In such embodiments the first discrete test sites and the second discrete test sites can be individually encoded. Suitable test sites include a planar microarray, a microparticle, a cell, a microdroplet, a nanodroplet, a femtodroplet, a micelle, a molecule, and a molecular complex.

Another embodiment of the inventive concept is method for improving the dynamic range of a biological binding assay by contacting a first test surface that includes a first capture molecule with a sample in a first volume, where the sample comprises a first target molecule that binds to the first capture molecule and also includes a second target molecule. This first volume provides a first sample dilution. The first test surface and the sample are incubated for a first period of time that is sufficient for the formation of a first complex that includes the first capture molecule and the first target molecule. A second volume, which includes a second test surface, is then added to the first volume, thereby generating a second sample dilution. This second test surface includes a second capture molecule, and in some embodiments the second volume exceeds to the first volume. The second test surface and the sample (diluted in the second sample dilution) is incubated for a second period of time sufficient for the formation of a second complex that includes the second capture molecule and the second target molecule. First and second signals are then obtained from the first complex and a second signal from the second complex, respectively. In some embodiments the first test surface comprises a first population of microparticles and the second test surface comprises a second population of microparticles. In some embodiments the second target molecule is present in the sample at a concentration that exceeds that of the first target molecule. In some embodiments the first target molecule and the second target molecule are not distinguishable, and the first capture molecule and the second capture molecule have the same specificity. In such embodiments the dynamic range of an assay directed to a single analyte is extended. In some embodiments the first signal and/or the second signal can be quantified using the method described above in order to further extend the dynamic range of the biological assay(s).

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1A shows a dose/response curve produced for IL-1β. FIG. 1B shows a dose/response curve produced for IL-10. FIG. 1C shows a dose/response curve produced for IFN-γ. FIG. 1D shows a dose/response curve produced for IL-8. FIG. 1E shows a dose/response curve produced for hMCP-1. FIG. 1F shows a dose/response curve produced for IL-4. FIG. 1G shows a dose/response curve produced for IL-6.

DETAILED DESCRIPTION

Figure 1A:
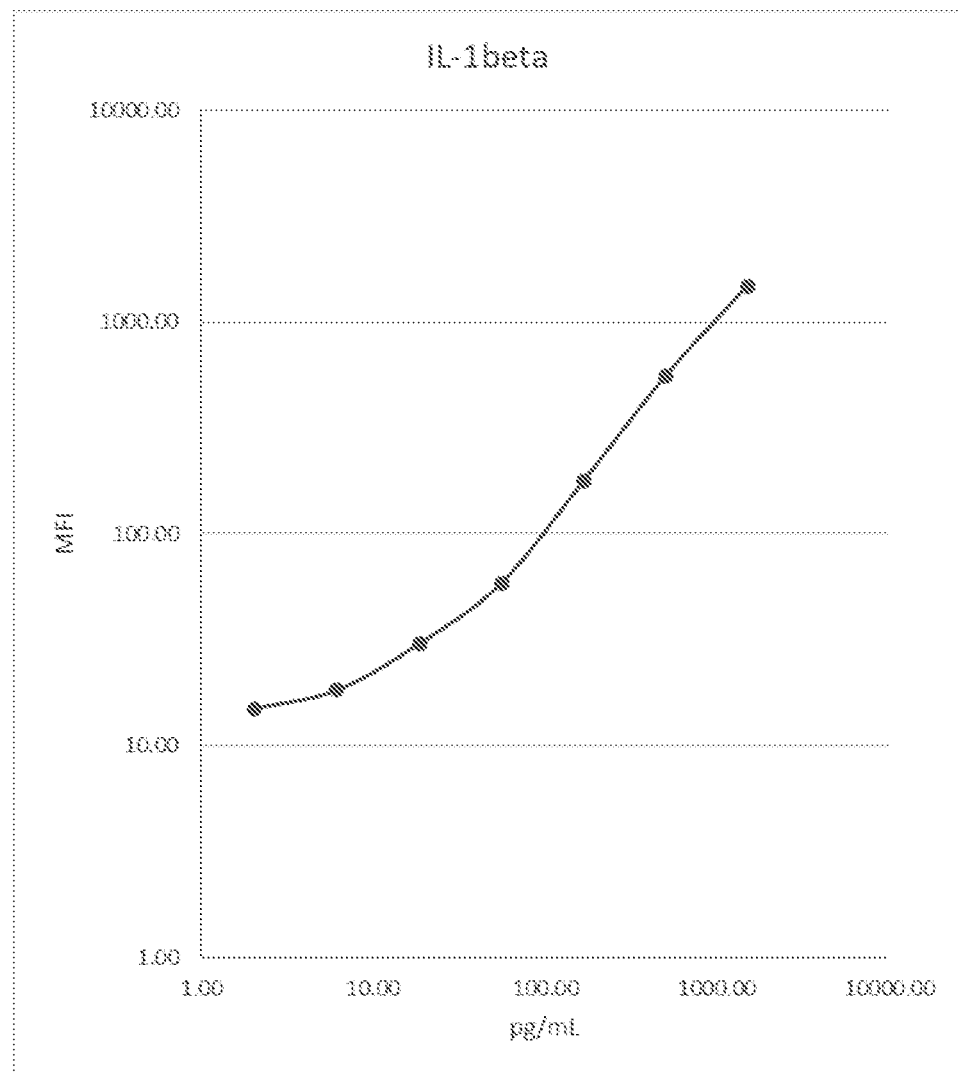
FIGS. 1A to 1G show dose response curves for median fluorescence intensity (MFI) of different microparticle-based cytokine assays performed in concert with a C-reactive protein (CRP) assay, using two different sample dilutions applied in a serial fashion in the same test well. Cytokine assay reagents were applied in an initial incubation at low sample dilution (1:3).

The following description includes information that may be useful in understanding the present invention. It is not an admission that any of the information provided herein is prior art or relevant to the presently claimed invention, or that any publication specifically or implicitly referenced is prior art.

The inventive subject matter provides apparatus, systems and methods in which an assay that provided that is performed using a plurality of discrete test regions. Suitable test regions include microparticles, spatially defined portions of a planar array, droplets (including microdroplets and/or femtodroplets) in an emulsion and/or suspension, individual pixels within a digitized image of a test region, cells, individual molecules in solution, and/or results that are otherwise encoded to represent a distinct region or volume of space. The discrete test regions are individually characterized for a signal intensity originating from recognition of an analyte of interest within the discrete test region. All or some of the discrete test regions utilized in testing of a test sample are subject to analysis (for example, in a flow cytometer) to determine analyte-specific signal intensity. The analyte-specific signal intensities of the discrete test regions are used to both perform a statistical analysis of the signal intensities of the tested population of discrete test regions and to determine if each discrete test region characterized includes the analyte in a binary fashion (i.e. positive or negative "digital" data). The digital data can be used to derive a proportion of discrete test regions that include analyte relative to those that do not. For example, a gating signal intensity value indicates a positive result for the presence of an analyte for an individual test region (e.g. a microparticle).

The percentage of the particle population that meets this criteria can be related to analyte concentration. For example, at moderate to high analyte concentrations essentially all test regions would indicate the presence of the analyte, corresponding to 100% occupancy. As the concentration of analyte decreases an increasing percentage of individual test sites will provide a signal indicating that no analyte was detected by that test site, and the occupancy decreases. For example, if 20% of the individual test sites characterized indicate that they did not identify the presence of analyte the occupancy would be considered to be 80%. For digital quantitation purposes a correlation can be established between the degree of occupancy and the concentration of the analyte once the occupancy is less than 100% but above background levels. For example, below a pre-determined cutoff value (for example, about 90% occupancy) such digital data can be used to calculate the concentration of analyte in the test sample. Above the pre-determined cutoff value the statistical data gathered from the population of discrete test regions characterized can be used to determine the concentration of analyte in the test sample. In a preferred embodiment the discrete test regions can be formulated (for example, through choice of antibody and/or antibody content) such that these ranges overlap and provide a continuous measuring range.

One should appreciate that the disclosed techniques provide many advantageous technical effects including providing an assay with an extended dynamic range relative to a conventional assay using signal intensity derived from a bulk solution, statistical calculation of mean signal intensity from a population of individual test results, and/or a binary categorization of individual members of a population of test results.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Inventors contemplate that the systems and methods described herein are applicable to a wide variety of biological assay formats, which can be based on the formation of a variety of biologically-derived molecules that pair specifically to act as binding partners. Suitable binding partners include immunoglobulins, lectins, cell surface receptors, aptamers, and nucleic acids. In some embodiments the biological assay can be an immunoassay, for example a direct (e.g. "sandwich") or competitive assay utilizing a labeled antibody or antibody analog (e.g. antibody fragment, single chain antibody, recombinant antibody, etc.) that binds (either directly or indirectly) to the analyte of interest and/or a labeled analyte form of the analyte of interest that is competed from a discrete test site by analyte in the sample being tested. Suitable labels include fluorescent molecules, luminescent molecules, phosphorescent molecules, chromophores, microparticles, metal particles or colloids, enzymes, and nucleic acids. In some embodiments such labels are incorporated directly by covalent attachment and/or genetic manipulation. In other embodiments such labels are incorporated through affinity means, such as through the use of biotin (or a biotin analog) and avidin/streptavidin, through the use of protein A and/or G, and/or through the use of labeling antibodies directed to components of the assay system.

In other embodiments systems and methods of the inventive concept are directed to nucleic acid binding and/or amplification assays. Such assays can include one or more polynucleotides that are at least partially complementary to a nucleic acid sequence representing or associated with a nucleotide sequence of interest. In such embodiments a detectable signal indicating the presence of the polynucleotide of interest can be generated by any suitable means, including binding or displacement of a probe sequence carrying a label, complex formation between a dye and a nucleic acid structure (e.g. a double helical region), etc. Suitable labels include fluorescent molecules, luminescent molecules, phosphorescent molecules, chromophores, microparticles, metal particles or colloids, enzymes, nucleic acids, and mass labels. In some embodiments such labels are incorporated directly by direct synthesis, covalent attachment, and/or genetic manipulation. In other embodiments such labels are incorporated through affinity means, such as through the use of biotin (or a biotin analog) and avidin/streptavidin, through the use of protein A and/or G, and/or through the use of labeling antibodies directed to components of the assay system.

Members of a binding partner pair can be localized to a test site, such as an encoded particle suitable for flow cytometry or a distinguishable site on a test surface, by any suitable means. Typically this can be accomplished by noncovalent binding (e.g. adsorption), covalent coupling (e.g. through available amine, sulfhydryl, or aldehyde groups on the binding partner molecule), or indirect coupling (e.g. through the use of protein A/G, streptavidin/avidin:biotin pair formation, etc.). Numerous coupling chemistries and protocols are known in the art. Examples of suitable coupling approaches include coupling of amine groups through hydroxysuccinimide or N-hydroxysuccinimide esters, sulfhydryl groups through N-ethylmaleimide groups, coupling of hydroxyl, amine, or sulfhydryl groups via epoxide groups, and coupling of aldehyde groups (e.g. produced through oxidation of carbohydrates or carbohydrate side chains of glycoproteins) via hydrazide groups.

In other embodiments systems and methods of the inventive concept are directed to cell based assays. Such assays can, for example, include cells that produce a measurable change in a signal intensity in the presence of an analyte of interest. In such embodiments individual cells can act as discrete test sites, which can in turn be identified as such through the identification of specific cell surface markers. Such cells can be in suspension or grown as a layer on a surface. In some embodiments the cells can be genetically modified to incorporate reporting constructs that generate a detectable signal. Suitable signals include fluorescence, phosphorescence, luminescence, and/or enzyme activity. In some embodiments cells in suspension can be characterized using a flow cytometer, where cells presenting as a layer on a surface can be characterized using a microscope system (which can in turn provide a digital image).

As noted above, a wide variety of discrete test sites are suitable for use in systems and methods of the inventive concept. In some embodiments discrete test sites can be a collection of individual reactive sites on a planar microarray. Such test sites can be individually identified (i.e. encoded) by their position on the microarray. Alternatively, such arrays can be assembled by permitting microparticles or other discrete bodies to settle or assemble on a planar or essentially planar surface. In such embodiments the microparticles or other discrete bodies can include identifying features. In such embodiments results can be characterized using a digital imaging system accompanied by appropriate image analysis software In other embodiments discrete test sites can be a collection of microparticles held in suspension. Such microparticles can be identified by incorporation of one or more detectable dyes (which are selected so that they do not interfere with the analyte-specific signal), size, density, diffraction pattern, response to magnetic field, and/or configuration. Such a collection of microparticles can, for example, be characterized using a flow cytometer.

In other embodiments discrete test sites can be a collection of micelles or droplets (such as microdroplets, nanodroplets, and/or femtodroplets) held as a suspension or emulsion. Such discrete test sites can be identified by incorporating one or more detectable labels within the micelle or droplet. Such a collection of micelles or droplets can, for example, be characterized using a flow cytometer or using a microchannel device.

In still other embodiments discrete test sites can be a collection of individual molecules or molecular complexes held in solution. Such molecules or molecular complexes can be identified by incorporation of one or more detectable labels associated with the molecule or molecular complex.

In still other embodiments discrete test sites can be a collection of pixels obtained from a digital image of a bulk test site. For example, if an immunoassay is performed on a test surface and produces a visible signal a digital image can be obtained of that test surface that includes signal intensity data related to the concentration of the analyte of interest. The digital image includes pixels, each of which represent a discrete region within the overall test surface. In some embodiments of the inventive concept such individual pixels (or defined collections of pixels) can be considered and analyzed as discrete test sites in order to gain the benefits of systems and methods of the inventive concept.

In a preferred embodiment, the biological assay is an immunoassay that is performed on the surface of a collection of microparticles that are held in suspension. The immunoassay provides, through the use of labeled antibodies, a fluorescent signal that (in a direct assay) is retained on the particles if the analyte of interest is present. Such microparticles can be encoded by the integration of one or more fluorescent dye(s) that provide(s) a signal that is distinctive from the analyte-specific signal in order to identify the microparticles. Such microparticle can also be encoded by size. In some embodiments different populations of microparticles are applied to a single sample in order to provide results for more than one analyte species from a single assay (i.e. a multiplexed assay). In such a preferred embodiment results are preferably obtained utilizing a flow cytometer configured to identify and obtain analyte-specific signal data from individual microparticles as they pass through the instrument.

Analyte-specific signal data is subjected to at least two different analytical operations. In a statistical operation the collected data is aggregated and an estimate of "typical" discrete test site data is generated from the aggregated data. For instance, a frequency distribution of analyte-specific signal intensity from the collection of discrete test sites can be generated and a mean or median value determined and reported from this aggregated data. In a distinct, digital operation individual discrete test sites are determined to either include the analyte of interest (i.e. a "positive" discrete test site) or lack the analyte of interest (i.e. a "negative" discrete test site) based on a measurement of analyte-specific signal associated with the individual discrete test site. The relative amount of positive discrete test sites to negative discrete test sites is then determined (for example, using a ratio) to generate a digital result.

In systems and methods of the inventive concept the statistical and the digital results are combined to provide an aggregate result. The aggregate result is highly dependent on the digital results at low concentrations of the analyte of interest, for example where the relative amount of positive discrete test sites is about 90% or less of the total discrete test sites characterized. If the relative amount of positive discrete test sites exceeds this (or another applicable cutoff value) the aggregate result is highly dependent on the statistical result. This effectively increases the dynamic range of the biological assay. In some embodiments the dynamic range is about 2-fold, 5-fold, 10-fold, 25-fold, 50-fold, 100-fold, or greater than 100-fold of that of the same biological assay performed using only statistical or only digital data.

Table 1 shows typical results for a microparticle-based immunoassay directed to IL-10.

TABLE 1

| Mean Fluorescence Intensity (MFI) | Gated Negative Events % | Occupancy % | Nominal Concentration of IL-10 (pg/mL) |
|---|---|---|---|
| 327.81 | 0% | 100% | 500.00 |
| 151.25 | 0% | 100% | 166.67 |
| 56.23 | 0% | 100% | 55.56 |
| 23.93 | 0% | 100% | 18.52 |
| 7.84 | 0% | 100% | 6.17 |
| 3.02 | 38.20% | 61.8% | 2.06 |
| 1.50 | 62.79% | 37.21% | 0.69 |
| 1.60 | 69.88% | 30.12% | 0.00 |
| 1.09 | 89.66% | 10.34% | Blank |

As shown, statistical data (median fluorescence intensity or MFI) derived from a population of immunoassay microparticles fails to provide differentiation between concentration standards with concentrations below 2.06 pg/mL and only minor differences between 2.06 pg/mL and 6.17 pg/mL standards. Digital data (in the form of gated % of microparticles), however, shows a large distinction between 2.06 pg/mL and 0.69 pg/mL standards and clear distinction between the 0.69 pg/mL and 0.00 pg/mL standards. The aggregated results provide a continuous measuring range from at least 0.69 pg/mL to 500.00 pg/mL.

Table 2 shows the results of a similar study where TNFα concentration was determined. As shown, statistical data fails to provide differentiation between standards containing less than 2.47 pg/mL, whereas digital data provides clear distinction between concentration standards down to 0.27 pg/mL. The aggregate data provide a continuous dynamic range from at least 0.27 pg/mL to 200.00 pg/mL, representing an approximately 10-fold improvement over the use of statistical or digital data alone.

TABLE 2

| Mean Fluorescence Intensity (MFI) | Gated Negative Events % | Occupancy % | Nominal Concentration of TNF-α (pg/mL) |
|---|---|---|---|
| 166.98 | 0% | 100% | 200.00 |
| 85.52 | 0% | 100% | 66.67 |
| 37.52 | 0% | 100% | 22.22 |
| 13.34 | 1.32% | 98.68% | 7.41 |
| 5.19 | 27.84% | 72.16% | 2.47 |
| 2.31 | 62.35% | 37.65% | 0.82 |
| 2.19 | 68.18% | 31.82% | 0.27 |
| 1.45 | 84.29% | 15.71% | 0.00 |
| 1.24 | 100.00% | 0% | Blank |

Table 3 shows the results of another study, utilizing an assay directed to IL-6. As shown, statistical data fails to provide differentiation between standards containing less than 12.35 pg/mL, whereas digital data provides clear distinction between concentration standards down to 1.37. The aggregate data provide a continuous dynamic range from at least 1.37 pg/mL to 1,000 pg/mL, representing an approximately 10-fold to 100-fold improvement over the use of statistical or digital data alone.

TABLE 3

| Mean Fluorescence Intensity (MFI) | Gated Negative Events % | Occupancy % | Nominal Concentration of IL-6 (pg/mL) |
|---|---|---|---|
| 388.91 | 0% | 100% | 1000.00 |
| 199.89 | 0% | 100% | 333.33 |
| 87.38 | 0% | 100% | 111.11 |
| 39.95 | 0% | 100% | 37.04 |
| 18.11 | 1.75% | 98.25% | 12.35 |
| 8.43 | 41.82% | 58.18% | 4.12 |
| 5.23 | 71.70% | 28.30% | 1.37 |
| 3.92 | 94.34% | 5.66% | 0.00 |
| 3.82 | 96.30% | 3.70% | Blank |

Table 4 shows the results of GM-CSF determination using systems and methods of the inventive concept; Table 5 shows the results from a number of populations of microparticles exposed to a negative (0 pg/mL) control sample. As shown statistical data does differentiate between standards having concentrations of less than 12.35 pg/mL GM-CSF, whereas digital data provides differentiation between standards having down to 1.37 pg/mL GM-CSF. Repeated determinations using a negative control indicate that a "negative" microparticle content of about 90% or greater can be considered to be background noise.

TABLE 4

| Mean Fluorescence Intensity (MFI) | Gated Negative Events % | Occupancy % | Nominal Concentration of GM-CSF (pg/mL) |
|---|---|---|---|
| 562.34 | 0.00% | 100.0% | 1000.0 |
| 406.79 | 0.00% | 100.0% | 333.33 |
| 191.1 | 0.00% | 100.0% | 111.11 |
| 83.54 | 0.00% | 100.0% | 37.04 |
| 36.19 | 1.65% | 98.4% | 12.35 |
| 20.54 | 19.72% | 80.3% | 4.12 |
| 14.86 | 65.00% | 35.0% | 1.37 |
| 12.19 | 98.48% | 1.5% | Blank |

TABLE 5

| Mean Fluorescence Intensity (MFI) | Gated Negative Events % | Occupancy % |
|---|---|---|
| 12.30 | 86.61% | 13.4% |
| 12.86 | 95.24% | 4.8% |
| 12.98 | 89.15% | 10.9% |
| 12.75 | 94.44% | 5.6% |
| 12.19 | 90.68% | 9.3% |
| 12.08 | 98.11% | 1.9% |
| 12.19 | 92.47% | 7.5% |
| 12.30 | 90.26% | 9.7% |
| 12.41 | 91.6% | 8.4% |
| 12.41 | 88.24% | 11.8% |
| 12.41 | 95.04% | 5.0% |
| 12.30 | 93.75% | 6.3% |
| 12.41 | 91.79% | 8.2% |
| 11.76 | 93.13% | 6.9% |
| 12.30 | 89.78% | 10.2% |
| 12.41 | 91.79% | 8.2% |
| 11.76% | 93.13% | 6.9% |
| 12.30 | 89.78% | 10.2% |
| 11.86 | 91.89% | 8.1% |
| 11.65 | 93.28 | 6.7 |
| 12.41 | 88.79 | 11.2 |
| 12.19 | 92.25% | 7.8% |

In another embodiment of the inventive concept analyte mixtures in which one or more analyte(s) is/are present at a large (e.g. greater than 5-fold, 10-fold, 20-fold, 50-fold, 100-fold, 200-fold, 500-fold, 1,000-fold, or more than 1,000-fold) excess or one or more second analytes, and in which both analytes are characterized simultaneously. Such multiplex assays are performed using the same test vessel and with a common set of reagents, etc. for all analytes tested. As such in typical multiplex assays the various analytes are characterized within similar measuring ranges. In some instances, however, it is desirable to measure different analytes within the same sample where those analytes are present at significantly different concentrations. For example, cytokines are typically present in small amounts (e.g. about 1-100 pg/mL) in human serum whereas C-reactive protein is typically present in larger amounts (e.g. ng/mL to μg/mL quantities). Since C-reactive protein (CRP) and certain cytokines are also inflammation markers it is desirable to quantify them from the same sample, and preferably from the same assay.

In such embodiments of the inventive concept as applied to biological binding assays (e.g. immunoassays, hybridization assays, etc.) a first binding partner with a specific affinity for a first analyte present at low concentrations is provided in a reagent mixture. Such a first binding partner is coupled to or otherwise associated with a first analyte identifier, for example a fluorescently labeled microparticle that can be provided in a first liquid suspension. The first binding partner is exposed to a sample containing a mixture of analytes, including the first analyte, at a relatively low sample volume to first liquid suspension ratio (e.g. from 2:1 to 1:5) and incubated for a period of time sufficient to allow molecules of the first analyte in the sample to complex with microparticles carrying the first binding partner. The time required for this is a function of the avidity of the first binding partner, concentration of the first analyte, temperature, etc., and can range from about 15 minutes to 24 hours at temperatures ranging from 1° C. to 50° C. or higher (for example, in nucleic acid binding assays).

Following this initial binding step a suspension of a second binding partner (for example, a microparticle suspension of microparticle-coupled second binding partner) is added to this mixture at a volume sufficient to provide a relatively high sample volume:total reagent volume dilution (e.g. from 1:10 to 1:1,000). This step effectively reduces the concentration of a second, abundant analyte in the sample into a range that permits characterization by second reagent. At the same time, the presence of the second binding partner only at this higher dilution effectively prevents saturation of the second binding partner. This lack of saturation provides a more linear dose/response curve than would be afforded by exposure of the second binding partner to extremely high concentrations of the second analyte, as it provides partial occupancy of the total population of second binding partners over a wider range of second analyte concentrations.

After a second incubation period suitable for forming complexes between the second, abundant analyte and the second binding partner the extent to which first analyte:first binding partner and second analyte:second binding partner complexes have formed can be characterized, for example by the addition of second, labeled antibodies or probe nucleic acid sequences followed by optical characterization (e.g. in fluorescence activated cell sorter or similar device). In some embodiments this second incubation period is shorter than the first incubation period. In other embodiments the second incubation period is similar to the first incubation period. In still other embodiments the second incubation period is longer than the first incubation period. Similarly, the first and second incubation periods can take place at similar or different temperatures. In some embodiments the addition of the second binding partner is accompanied by components that modify the pH, ionic strength, and/or ionic composition of the reaction mixture. For example, in a nucleic acid binding assay the temperature and ionic strength of the reaction mixture during the second incubation can be modified from that of the first incubation in order to adjust hybridization efficiency and/or fidelity.

Surprisingly, Inventors have found that at least some of the first analyte:first binding partner complexes established in the first incubation are not lost following dilution, despite the expectation of re-equilibration at significantly lower free first analyte concentrations resulting from addition of the second volume containing the second binding partner. This allows generation of chronologically separated dose/response curves representing two different sample dilutions within a single multiplexed assay.

In such a method a first volume of an aqueous suspension of one or more high sensitivity bead-based capture reagents (for example, beads conjugated with high affinity antibodies specific for analytes present at low concentrations) can be added to a test well or vessel. In some embodiments the liquid portion of the dispensed suspension can be removed (for example, through the use of a filter microwell plate) in order to minimize subsequent dilution of an applied sample. A volume of sample can then be added to the high sensitivity bead-based capture reagents, along with a volume of assay buffer, and the minimally diluted sample incubated with the high sensitivity bead-based reagents for a suitable period of time (for example, from 15 minutes to 24 hours) and temperature (for example, from 4° C. to 50° C. or higher). Typical dilutions of the sample in the volume represented by the high sensitivity bead-based reagent and the assay buffer during this initial capture incubation can range from about 10:1 to 1:10, and can be outside of this range in some applications.

Following the initial capture incubation a volume of a suspension containing one or more low sensitivity bead-based capture reagents (for example, beads conjugated with antibodies specific for analytes present in the sample at high concentrations) is added directly to the test well or vessel, resulting in dilution of both the sample and the high sensitivity bead-based reagents for a second capture incubation performed for a suitable period of time (for example, from 15 minutes to 24 hours) and at a suitable temperature (for example, from 4° C. to 50° C. or higher). The dilution of sample relative to the total volume represented by the assay buffer, high sensitivity-bead based reagent, and low-sensitivity bead-based reagent can range from about 1:10 to 1:100 or more during this second capture incubation. In some embodiments the second capture incubation is performed for a shorter period of time than the first capture incubation. Following the second capture incubation the amount of bound low abundance analyte and bound high abundance analyte can be characterized, for example by incubation with specific antibodies conjugated with detectable labels (e.g. biotin, fluorophores, etc.). Surprisingly, while conventional steady-state equilibrium models for noncovalent interactions suggest that such dilution should result in a loss of captured analyte from the high sensitivity bead-based reagent Inventors have found that such analyte is retained following dilution.

In an example of such an embodiment, 45 µL of a suspension of beads conjugated with specific antibodies to different cytokines were added to wells of a microplate and the suspending buffer removed. Following buffer removal 10 µL of assay buffer and 5 µL of a serum sample or serum-based cytokine calibrator were added to the wells, providing a sample dilution of 1:3 in assay buffer. After a first capture incubation for 1 hour at room temperature, 285 µL of a suspension of beads conjugated with antibody specific for CRP (a high abundance analyte) were added to the wells, providing a sample dilution of 1:60 in buffer+ reagents. After a second incubation for 30 minutes at room temperature liquid contents of the wells were removed and the beads were washed 3 times using wash buffer. It should be appreciated that no additional steps are necessary between the first and second capture incubations. 25 µL of a solution of biotinylated detection antibodies specific for the cytokines and CRP were added to each well, and incubated for 30 minutes at room temperature. Liquid contents of the wells were then removed and the beads washed 3 times with wash buffer before 25 µL of a streptavidin-PE solution was added to each well. After a 10 minute incubation at room temperature liquid contents of the wells were removed and the beads washed twice with wash buffer before analysis on a flow cytometer.

Figure 1B:
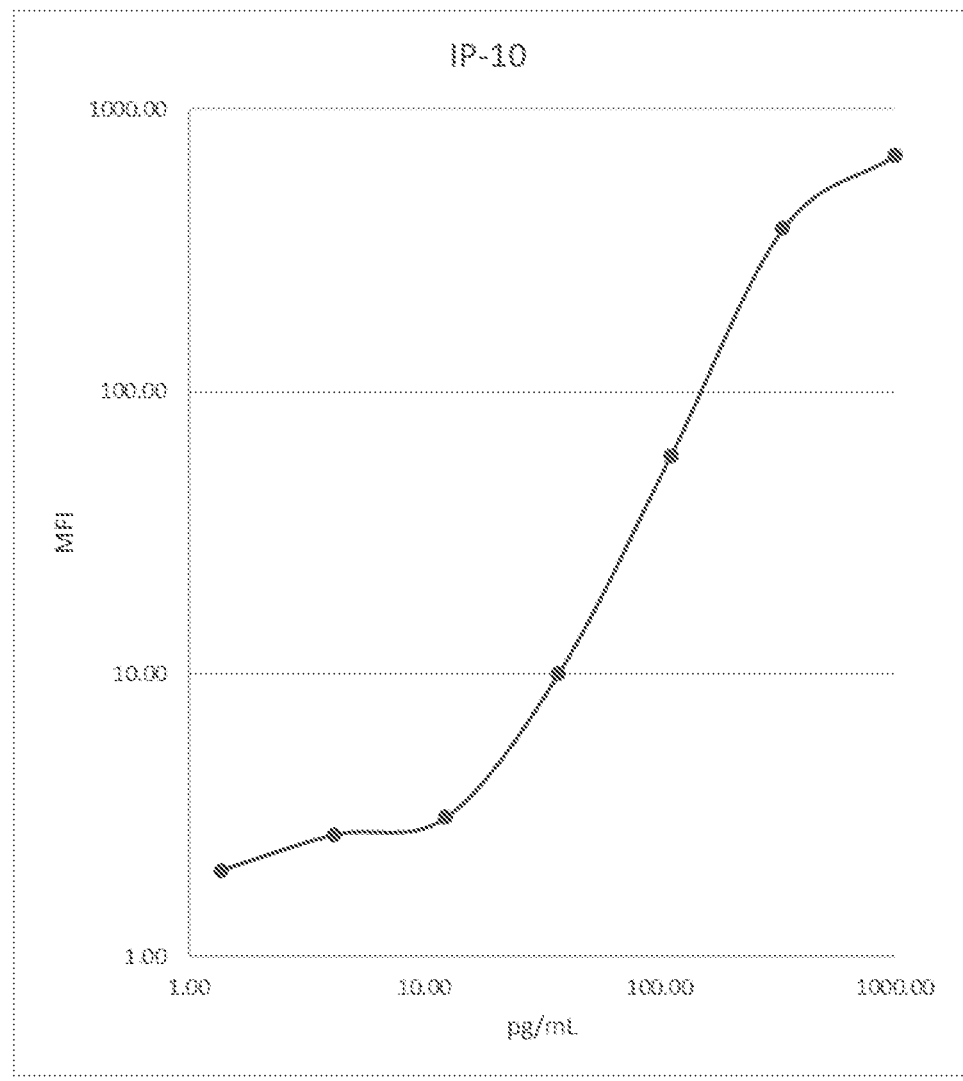
Figure 1C:
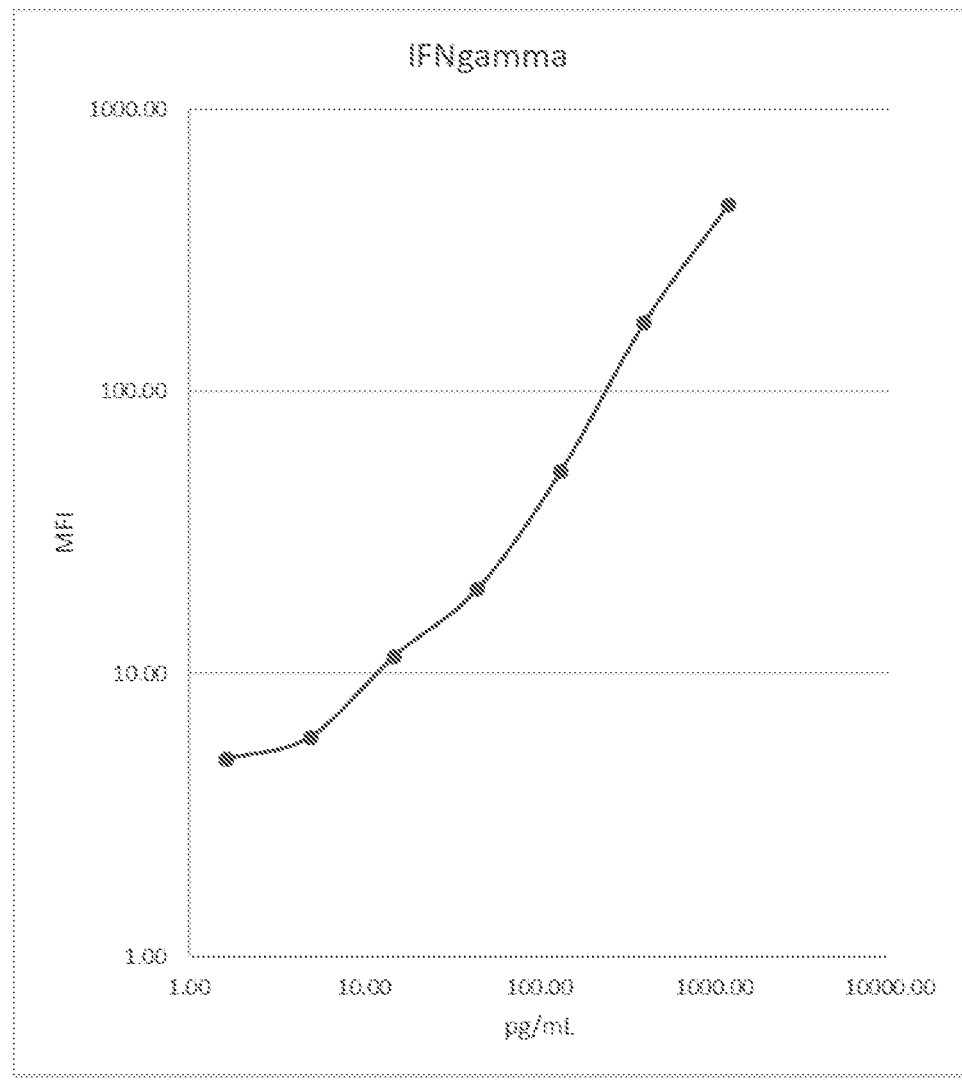
Figure 1D:
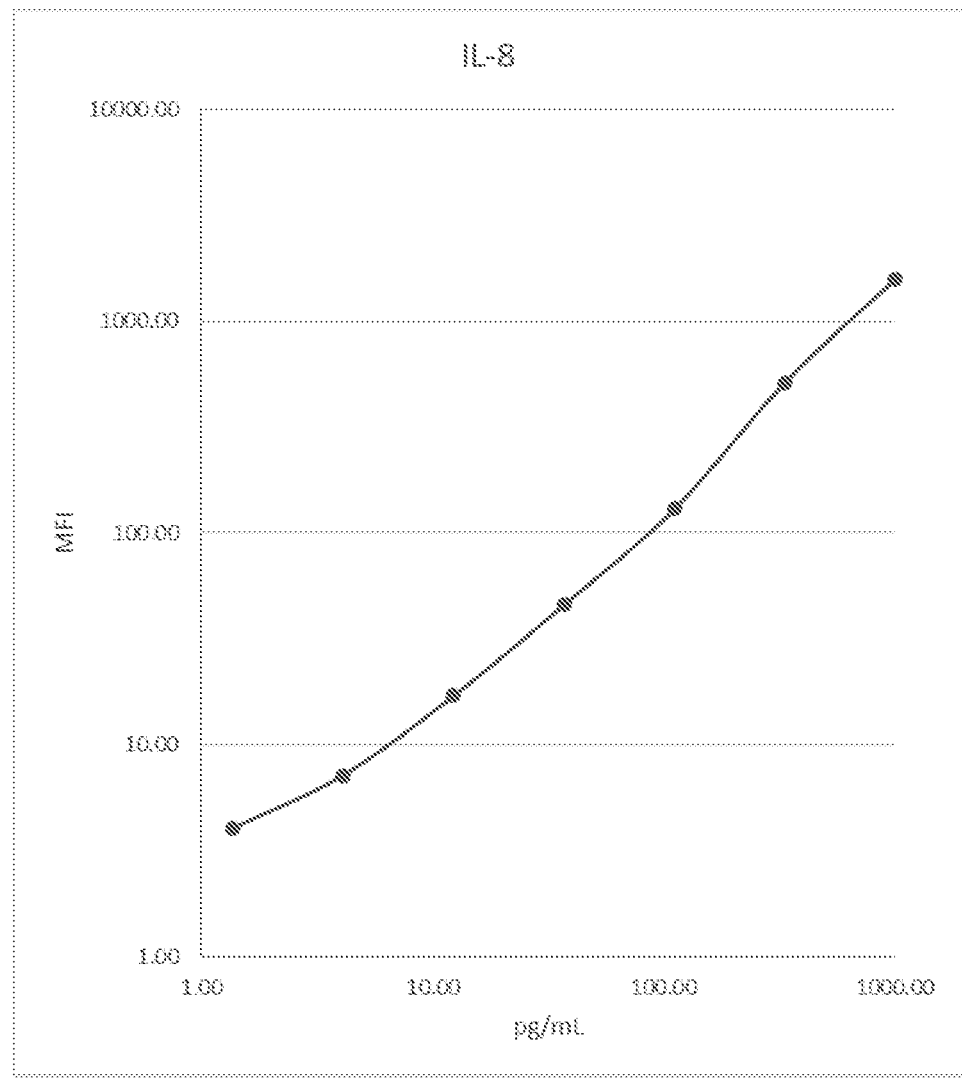
Figure 1E:
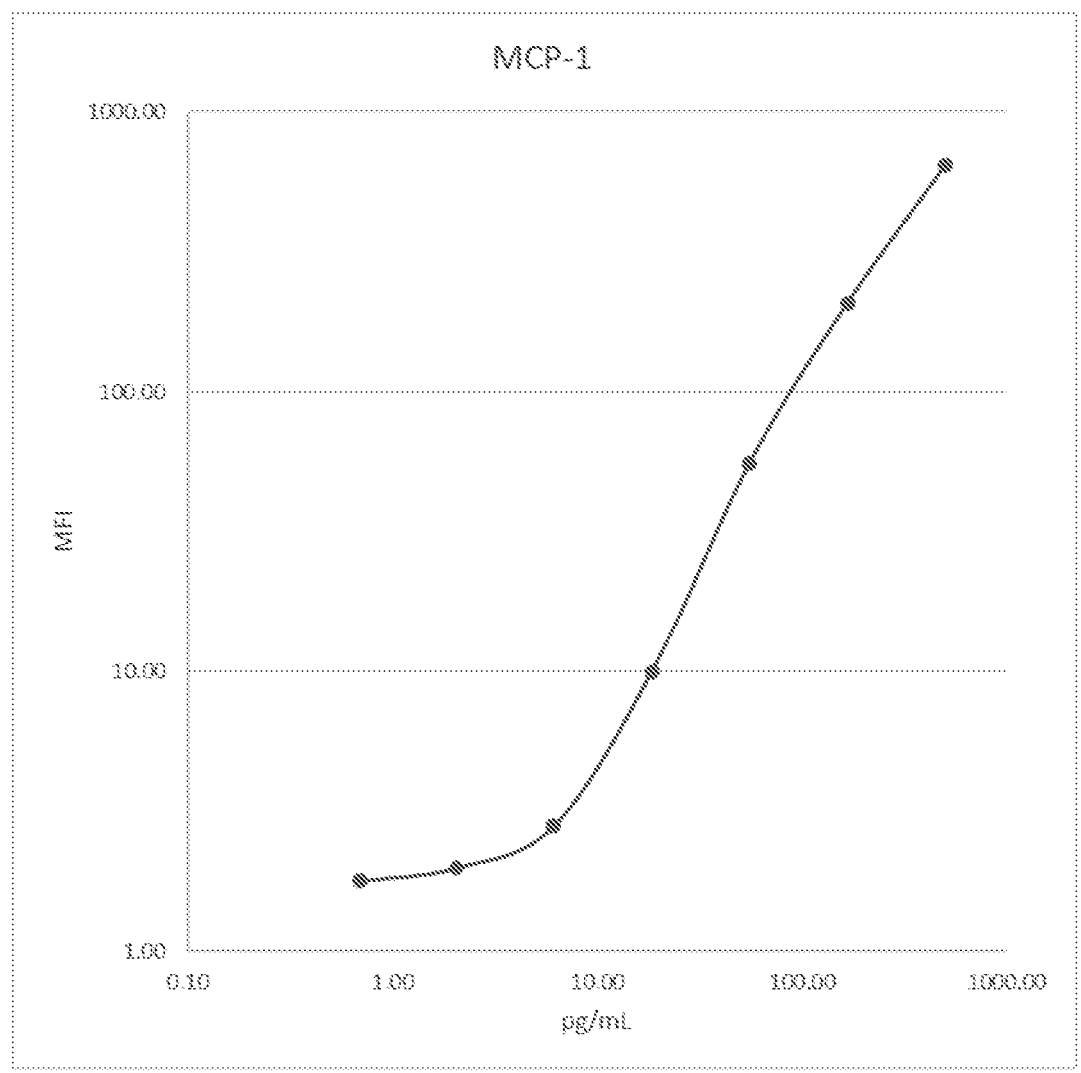
Figure 1F:
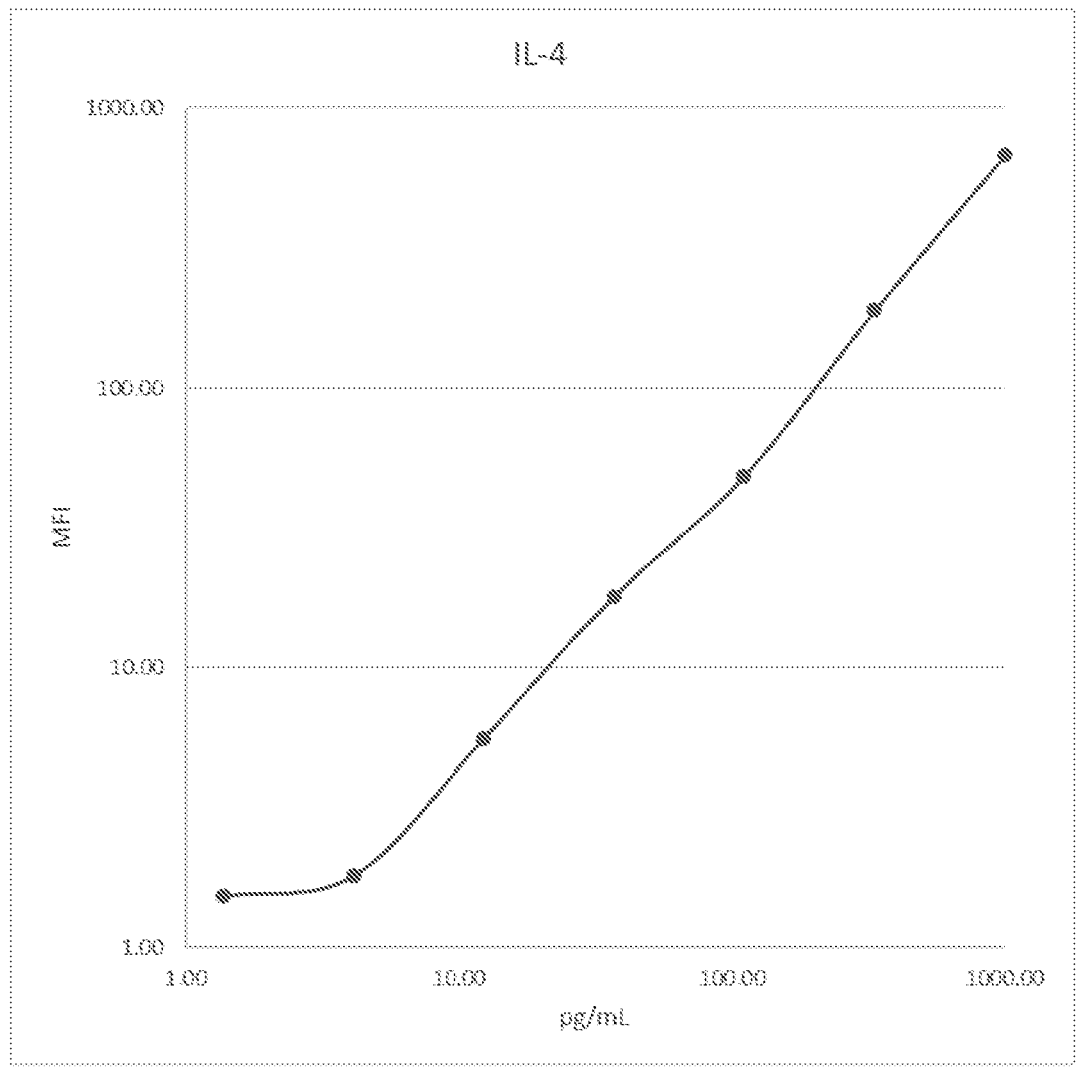
Figure 1G:
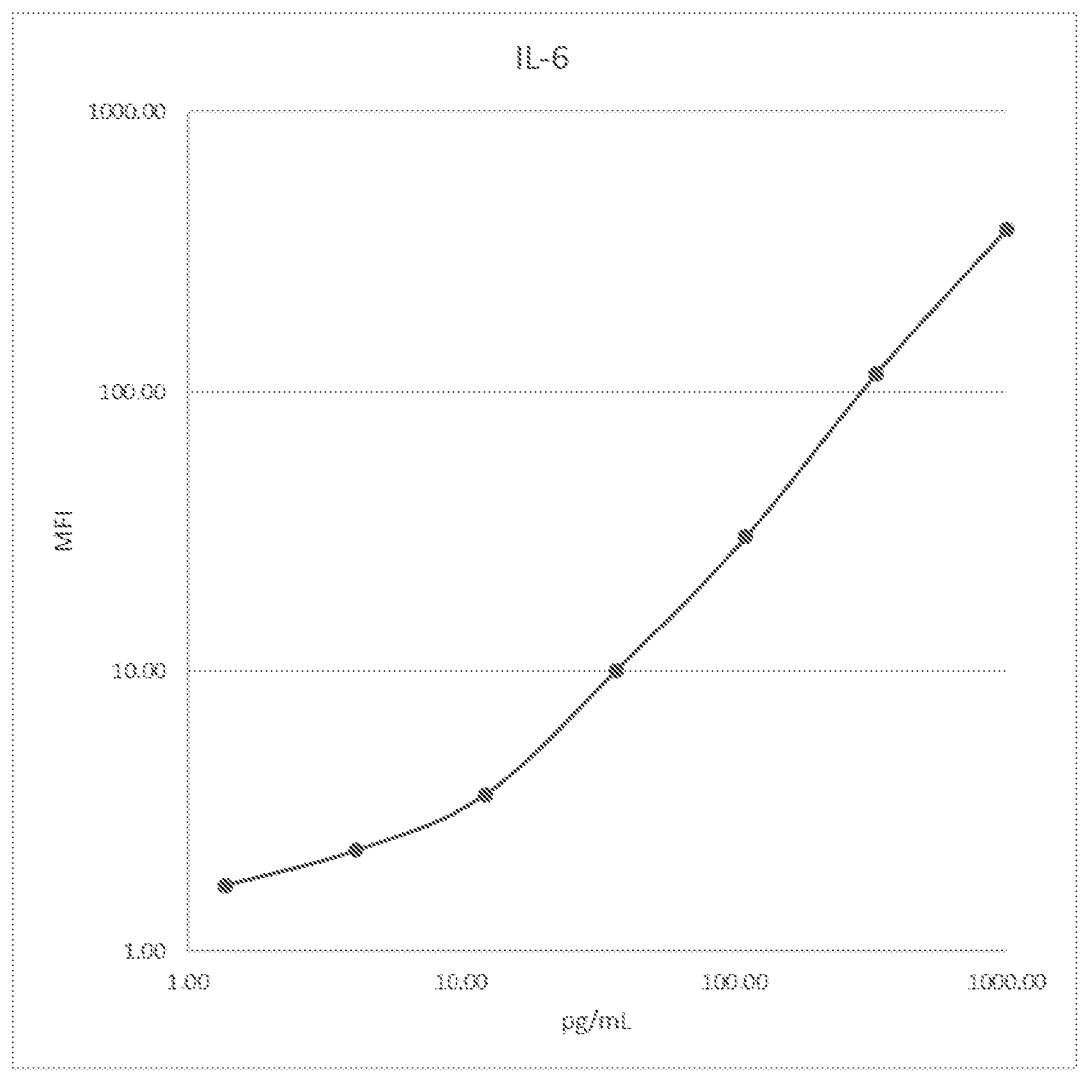
Figure 2:
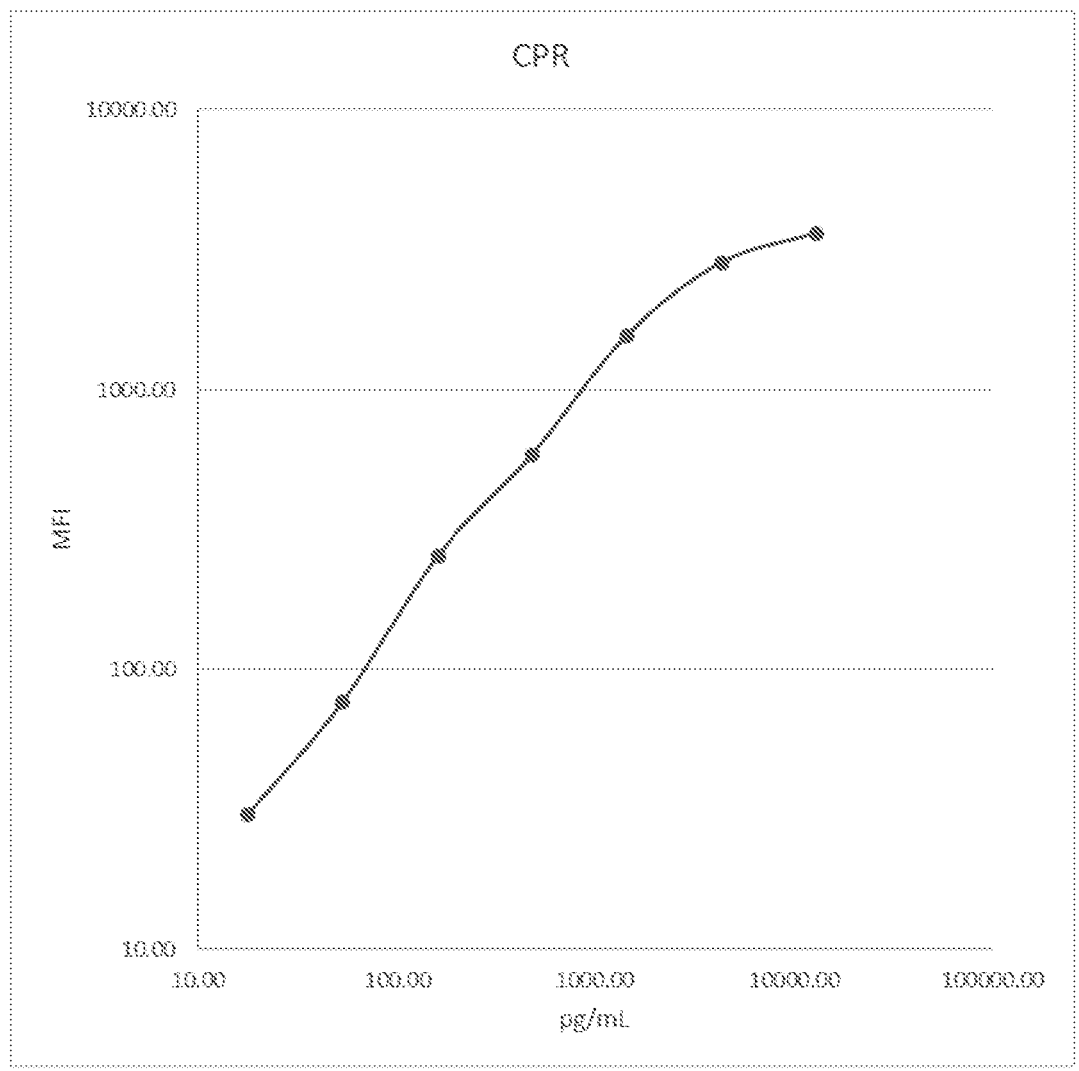
FIG. 2 depicts a dose/response curve for median fluorescence intensity (MFI) of the C-reactive protein (CRP) assay performed in concert with multiplexed cytokine assays, using two different sample dilutions applied in a serial fashion in the same test well. CRP assay reagents were provided after addition of the cytokine assay reagents, in a volume that provided a second sample dilution (1:60).

Typical results from such a study are shown in FIGS. 1A to 1G (low abundance analytes-cytokines) and FIG. 2 (high abundance analyte—CRP). FIG. 1A shows a dose/response curve produced for IL-1β; background fluorescence intensity was 14.07 MFI and the LDD about 2 pg/mL. FIG. 1B shows a dose/response curve produced for IP-10; background fluorescence intensity was 1.86 MFI and the LDD about 2-4 pg/mL. FIG. 1C shows a dose/response curve produced for IFN-γ; background fluorescence intensity was 5.09 MFI and the LDD about 5-10 pg/mL. FIG. 1D shows a dose/response curve produced for IL-8; background fluorescence intensity was 1.36 MFI and the LDD about 1-1.5 pg/mL. FIG. 1E shows a dose/response curve produced for human MCP-1 (hMCP-1); background fluorescence intensity was 1.00 MFI and the LDD about 2-5 pg/mL. FIG. 1F shows a dose/response curve produced for IL-4; background fluorescence intensity was 1.45 MFI and the LDD about 5-10 pg/mL. FIG. 1G shows a dose/response curve produced for IL-6; background fluorescence intensity was 1.45 MFI and the LDD about 5-10 pg/mL. FIG. 2 shows a dose/ response curve produced for CRP; background fluorescence intensity was 4.61 MFI and the LDD about 18 pg/mL. FIGS. 1A to 1G (representing low abundance analytes) show dose response curves with dynamic ranges of approximately about 1 to 500 pg/mL or about 10 to 1,000 pg/mL (depending upon the cytokine tested), whereas FIG. 2 (representing a high abundance analyte) shows a dose response curve with a dynamic range of approximately 18 to 13,000 pg/mL. Overall, an immunoassay range of over 5 orders of magnitude (considering that serum samples were diluted 60-fold for the CRP assay) was achieved in a single test well in this example of an embodiment of the inventive concept (e.g. a 5 to 6 order of magnitude dynamic range, such as 1-1.5 pg/mL to 780,000 pg/mL when dilution is taken into account). Inventor believes that, with the use of high resolution flow cytometry, assay dynamic range can be extended to 7 to 8 orders of magnitude or beyond using combined serial dilution and digital/statistical data analysis techniques.

It should be appreciated that more than two sets of capture reagents can be utilized, thereby generating three or more sample incubations at different dilutions in a single test well or vessel. In some embodiments different sets of capture reagents can be directed to the same analyte, utilizing capture phases with the same specificity but differentially labeled. Such embodiments can be utilized to quantify or characterize a single analyte that occurs over a very broad range of concentrations. For example, small sample dilution incubations can be performed with a first set of specific capture reagents quantify small concentrations of analyte, while large sample dilutions incubations can be performed with a second set of capture reagents having the same specificity but a different label that permits differentiation from the first capture reagent. At low concentrations of the analyte, capture reagents added at low dilution would provide useful data while the second set of capture reagents provided at high dilution would show little to no signal and could be disregarded. At high concentrations of the analyte the first set of capture reagents provided at low dilutions would be saturated and fail to provide useful information (and therefore disregarded), whereas the second set of capture reagents provided at high dilution would be able to provide useful data. In some embodiments, such sets of specific capture reagents can be directed to the same analyte but utilize different binding partners with different affinities and/or avidities.

In another embodiment of the inventive concept, the use of combined statistical and digital data analysis can be used in conjunction with successive sample dilution as described above to further extend assay range. Examples of this combined approach are provided in Tables 6 to Y, exemplary data for which was generated using an assay protocol as described above for FIGS. 1A to 1G and FIG. 2.

Table 6 shows both statistical data in the form of median fluorescence intensity (MFI) and digital data in the form of the gated % of beads for concentrations of IL-2 ranging from 0.00 to 100 pg/mL. The LDD provided for IL-2 in this successive sample dilution assay by MFI is about 11 pg/mL, whereas use of Gated % in this mixed format provides an LLD of about 1 pg/mL.

TABLE 6

| [IL-2] pg/mL | MFI | Gated Negative Events % |
|---|---|---|
| 100 | 46.14 | 0.00% |
| 33.33 | 23.71 | 8.15% |
| 11.11 | 14.07 | 32.12% |

TABLE 6-continued

| [IL-2] pg/mL | MFI | Gated Negative Events % |
|---|---|---|
| 3.70 | 6.98 | 71.83% |
| 1.23 | 6.49 | 85.71% |
| 0.41 | 6.21 | 94.00% |
| 0.14 | 6.85 | 93.51% |
| 0.05 | 6.32 | 98.61% |
| 0.00 | 6.32 | 98.36% |

Table 7 shows both statistical data in the form of mean fluorescence intensity (MFI) and digital data in the form of the gated % of beads for concentrations of IL-1β ranging from 0.00 to 100 pg/mL. The LDD provided for IL-1β in this successive sample dilution assay by MFI is about 1 pg/mL (consistent with the previous example), whereas use of Gated % in this mixed format provides an LLD of about 0.1 pg/mL. Based on replication of the assay protocol and LDD results using MFI the Inventor believes that an extended dose/response curve would replicate that shown in FIG. 1A.

TABLE 6

| [IL-1β] pg/mL | MFI | Gated Negative Events % |
|---|---|---|
| 100 | 132.16 | 0.00% |
| 33.33 | 125.21 | 0.00% |
| 11.11 | 57.77 | 0.00% |
| 3.70 | 21.29 | 9.23% |
| 1.23 | 7.04 | 36.75% |
| 0.41 | 3.22 | 70.00% |
| 0.14 | 2.71 | 85.83% |
| 0.05 | 2.57 | 88.80% |
| 0.00 | 2.04 | 90.68% |

Table 8 shows both statistical data in the form of median fluorescence intensity (MFI) and digital data in the form of the gated % of beads for concentrations of IL-22 ranging from 0.00 to 100 pg/mL. The LDD provided for IL-22 in this successive sample dilution assay by MFI is about 1 pg/mL, whereas use of Gated % in this mixed format provides an LLD of about 0.15 pg/mL.

TABLE 8

| [IL-22] pg/mL | MFI | Gated Negative Events % |
|---|---|---|
| 100 | 491.37 | 0.00% |
| 33.33 | 209.08 | 0.00% |
| 11.11 | 88.17 | 9.33% |
| 3.70 | 41.42 | 52.08% |
| 1.23 | 25.95 | 78.16% |
| 0.41 | 19.99 | 88.41% |
| 0.14 | 15.68 | 93.08% |
| 0.05 | 16.55 | 95.45% |
| 0.00 | 12.41 | 96.23% |

Table 9 shows both statistical data in the form of median fluorescence intensity (MFI) and digital data in the form of the gated % of beads for concentrations of IL-6 ranging from 0.00 to 100 pg/mL. The LDD provided for IL-6 in this successive sample dilution assay by MFI is about 11 pg/mL (consistent with the findings shown in FIG. 1G), whereas use of Gated % in this mixed format provides an LLD of about 0.1 pg/mL. Based on replication of the assay protocol and LDD results using MFI the Inventor believes that an extended dose/response curve would replicate that shown in FIG. 1G.

TABLE 9

| [IL-6] pg/mL | MFI | Gated Negative Events % |
|---|---|---|
| 100 | 173.09 | 0.00% |
| 33.33 | 67.93 | 2.44% |
| 11.11 | 24.36 | 2.53% |
| 3.70 | 7.43 | 22.99% |
| 1.23 | 2.53 | 72.73% |
| 0.41 | 2.21 | 83.76% |
| 0.14 | 2.04 | 89.58% |
| 0.05 | 2.05 | 93.81% |
| 0.00 | 12.41 | 94.89% |

Table 10 shows both statistical data in the form of median fluorescence intensity (MFI) for concentrations of CRP ranging from 0.00 to 13,000 pg/mL. The LDD provided for CRP in this successive sample dilution assay by MFI is about 6 pg/mL (consistent with the findings shown in FIG. 2).

TABLE 10

| [CRP] pg/mL | MFI |
|---|---|
| 13,000 | 3,421.60 |
| 4,333.33 | 3,013.50 |
| 1,444.44 | 1,995.68 |
| 481.48 | 821.22 |
| 160.49 | 321.45 |
| 53.50 | 122.98 |
| 17.83 | 57.77 |
| 5.94 | 27.38 |
| 0.00 | 8.51 |

It should be appreciated that a variety of assay formats can be utilize the serial dilution and/or digital/statistical data analysis approaches described above. For example, most binding/hybridization assays directed towards biomolecules (e.g. proteins, nucleic acids, etc.) are adaptable to microwell plates or other arrayed test site formats that are amenable to multiple additions of reagents to a single discrete test site and subsequent removal of spent reagents (e.g. by filtration, centrifugation, aspiration, etc.). In some embodiments a microfluidic/microchannel device can be used, in which flow channels of different sizes can be utilized to effect serial dilution. In such embodiments test sites can be discrete and suspendable (i.e. able to be suspended in a fluid test media under assay conditions and over the course of the assay), such as microparticles, micelles, emulsions, etc. For example, initial sample dilution and interaction with a first set of test microparticles can take place in a narrow, low volume channel that provides a relatively low sample dilution. After flowing for a period of time sufficient for the initial set of complexes to form this narrow, low volume channel can join with a wide, high volume channel carrying an additional set of test microparticles suspended in a volume of diluent. Subsequent mixing in a common wide, high volume channel provides a relatively low sample dilution useful for quantifying analytes at higher concentrations. Coupling the output of such a microfluidic/microchannel device to a flow cytometer permits combined digital/statistical quantitation as described above. In such embodiments the microfluidic/microchannel device can be a single use/disposable device; in other embodiments the microfluidic/microchannel device can be a multiple use device intended for use with two or more different samples.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of quantifying results of a biological assay comprising:
performing a first biological assay directed to a first analyte on a sample using a plurality of first discrete test sites, wherein the first biological assay provides a change in a first signal indicative of the presence of the first analyte;
deriving a plurality of quantities for the first signal, wherein each of the plurality of quantities is associated with the first signal observed from an individual first discrete test sites of a first population of the first discrete test sites;
determining, using at least a portion of the plurality of quantities, a first proportion, wherein the first proportion comprises an enumeration of the first discrete test sites indicating the presence of the analyte;
calculating a statistical distribution of the plurality of quantities derived from the first discrete test sites to derive a statistical value for the first signal; and
quantifying the mass of the first analyte in the sample using the first proportion when the first proportion falls within a first cutoff range of values for the first proportion, and using the statistical value of the first signal when the first proportion falls outside of the first cutoff range of values for the first proportion.

2. The method of claim 1, wherein the method further comprises:
performing a second biological assay directed to a second analyte on the sample using a plurality of second discrete test sites, wherein the second biological assay provides a change in a second signal indicative of the presence of the second analyte;
deriving a plurality of quantities for the second signal, wherein each of the plurality of quantities is associated with the second signal observed from an individual second discrete test sites of a second population of the second discrete test sites;
determining, using at least a portion of the plurality of quantities, a second proportion, wherein the second proportion comprises an enumeration of the second discrete test sites indicating the presence of the second analyte;
calculating a statistical distribution of the plurality of quantities derived from the second discrete test sites to derive a statistical value for the second signal; and
quantifying the mass of the second analyte in the sample using the second proportion when the second proportion falls within a second cutoff range of values for the second proportion, and using the statistical value of the second signal when the second proportion falls outside of the first cutoff range of values for the second proportion.

3. The method of claim 2, wherein the first discrete test sites and the second discrete test sites are individually encoded.

4. The method of claim 2, wherein the first biological assay and the second biological assay are performed simultaneously.

5. The method of claim 2, wherein the second cutoff range of values is selected to delineate a population in which less than 90% of the second discrete test sites include the second analyte.

6. The method of claim 2, wherein the first analyte and the second analyte are cytokines.

7. The method of claim 1, wherein the first discrete test site is selected from the group consisting of an element of a planar microarray, a microparticle, a cell, a microdroplet, a nanodroplet, a femtodroplet, a micelle, a molecule, and a molecular complex.

8. The method of claim 1, wherein the first biological assay is selected from the group consisting of an immunoassay, a nucleic acid amplification assay, an enzyme assay, and a biological activity assay.

9. The method of claim 1, wherein the first signal is selected from the group consisting of fluorescence, enzyme activity, absorbance, phosphorescence, and luminescence.

10. The method of claim 1, wherein the first cutoff range of values is selected to delineate a population in which less than 90% of the first discrete test sites include the first analyte.

11. The method of claim 1, wherein results are determined using a flow cytometer.

12. The method of claim 1, wherein the first biological assay is performed using a microfluidic or microchannel device.

13. A method for improving the dynamic range of a biological binding assay, comprising:
   contacting a first test surface comprising a first capture molecule with a sample in a first volume, wherein the sample comprises a first target molecule that binds to the first capture molecule and a second target molecule, and wherein the first volume comprises a first sample dilution;
   incubating the first test surface and the sample for a first period of time sufficient for the formation of a first complex comprising the first capture molecule and the first target molecule;
   adding to a second volume comprising a second test surface to the first volume, thereby generating a second sample dilution, wherein the second test surface comprises a second capture molecule and wherein the second volume exceeds to the first volume;
   incubating the second test surface and the sample for a second period of time sufficient for the formation of a second complex comprising the second capture molecule and the second target molecule; and
   obtaining a first signal from the first complex and a second signal from the second complex.

14. The method of claim 13, wherein the first test surface comprises a first population of microparticles and the second test surface comprises a second population of microparticles.

15. The method of claim 13, wherein the second target molecule is present in the sample at a concentration that exceeds that of the first target molecule.

16. The method of claim 13, comprising the additional step of washing the first and second test surfaces prior to obtaining the first and second signals.

17. The method of claim 13, wherein the first target molecule and the second target molecule are not distinguishable, and wherein the first capture molecule and the second capture molecule have the same specificity.

18. The method of claim 13, wherein the first test surface comprises a plurality of individual first discrete test sites, and wherein a change in a first signal is indicative of the presence of the first target molecule in the sample, and comprising the additional steps of;
   deriving a plurality of quantities for the first signal, wherein each of the plurality of quantities is associated with the first signal observed from an individual first discrete test sites of a first population of the first discrete test sites;
   determining, using at least a portion of the plurality of quantities, a first proportion, wherein the first proportion comprises an enumeration of the first discrete test sites indicating the presence of the first target molecule;
   calculating a statistical distribution of the plurality of quantities derived from the first discrete test sites to derive a statistical value for the first signal; and
   quantifying the mass of the first target molecule in the sample using the first proportion when the first proportion falls within a first cutoff range of values for the first proportion, and using the statistical value of the first signal when the first proportion falls outside of the first cutoff range of values for the first proportion.

19. The method of claim 13, wherein the first test surface and the second test surface are provided in a microfluidic or microchannel device.

* * * * *